(12) United States Patent
Voisin

(10) Patent No.: US 6,312,475 B1
(45) Date of Patent: Nov. 6, 2001

(54) PROSTHETIC ADAPTOR AND PROSTHETIC LIMB USING SAME

(76) Inventor: Jerome P. Voisin, 145 Agnes St., Houma, LA (US) 70363

(*) Notice: Subject to any disclaimer, the term of this patent is extended or adjusted under 35 U.S.C. 154(b) by 0 days.

(21) Appl. No.: 09/436,326

(22) Filed: Nov. 8, 1999

Related U.S. Application Data

(63) Continuation of application No. 08/961,693, filed on Oct. 31, 1997, now abandoned.
(60) Provisional application No. 60/029,691, filed on Oct. 31, 1996.

(51) Int. Cl.[7] .................................................. A61F 2/60
(52) U.S. Cl. ............................. 623/33; 623/38; 623/53; 264/101; 264/263
(58) Field of Search ............................. 623/33, 38, 901, 623/47, 53; 264/274, 571, 263, 101, DIG. 64

(56) References Cited

U.S. PATENT DOCUMENTS

| | | | |
|---|---|---|---|
| 3,422,462 | 1/1969 | Finnieston | 623/33 |
| 5,507,837 | 4/1996 | Laghi | 623/38 |
| 5,728,171 | * 3/1998 | Bryant et al. | 623/38 |

FOREIGN PATENT DOCUMENTS

| | | | |
|---|---|---|---|
| 2 101 254 | 7/1972 | (DE) | 623/38 |
| 353 510 | 2/1990 | (EP) | 264/274 |
| 1487 897 | 6/1989 | (RU) | 623/27 |

\* cited by examiner

Primary Examiner—David H. Willse
(74) Attorney, Agent, or Firm—Young & Basile, P.C.

(57) ABSTRACT

An adaptor which may be secured to the lower end of a lower limb prosthesis which would allow the lower limb prosthesis to be secured to an ankle joint or prosthetic foot with a mechanical locking or anchoring type of fixation. What is provided is the lower limb prosthesis which would include an upper socket portion for receiving the stump of the wearer, a limb portion which extends from the socket portion down to approximately the ankle portion of the wearer, and an adaptor portion. The adaptor portion would further include a triangulated base portion which would mate with the lower end of the prosthetic limb. There would be further included a second barb portion extending from the base portion, which would define an area between the barb portion extending from the base portion, so that when the adaptor is fabricated onto the limb through either a lamination process or a drape molding process, the adaptor is secured more tightly against the limb during the fabrication process. Further, there is included a threaded collar secured within a bore of the base portion, for threadingly engaging the base portion to the upper end of an ankle and/or prosthetic foot of the wearer.

26 Claims, 2 Drawing Sheets

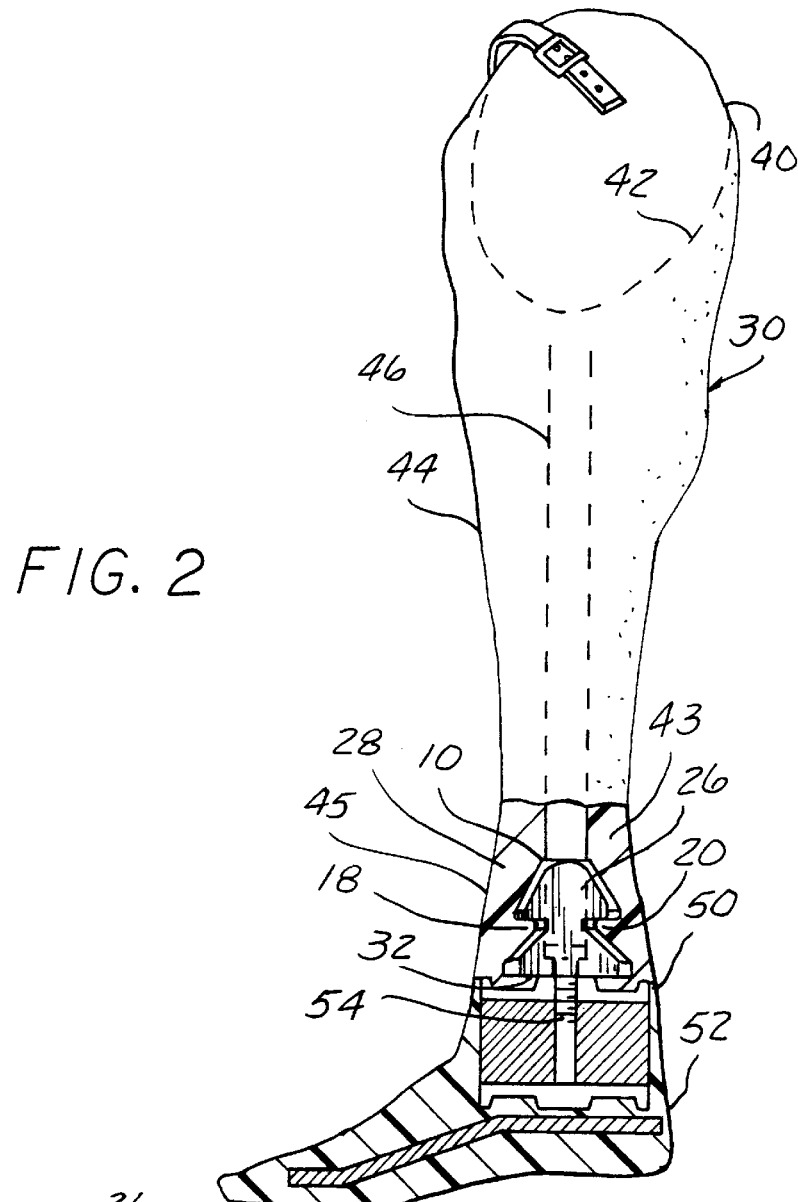
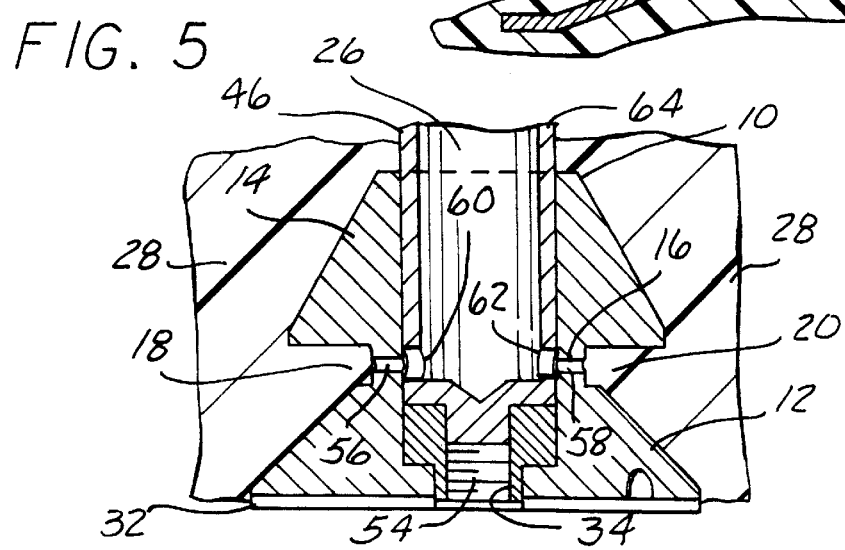

PROSTHETIC ADAPTOR AND PROSTHETIC LIMB USING SAME

RELATED APPLICATIONS

This application is a continuation of Ser. No. 08/961,693 filed Oct. 31, 1997 in the name of Jerome P. Voisin and entitled "PROSTHETIC ADAPTOR AND PROSTHETIC LIMB USING SAME", now abandoned, which is a continuation-in-part of provisional patent application Ser. No. 60/029,691 filed on Oct. 31, 1996 by Jerome P. Voisin and entitled "Improved Prosthetic Adaptor," the disclosure of which is hereby incorporated by reference in its entirety.

BACKGROUND OF THE INVENTION

1. Field Of The Invention

The present invention relates to prosthetic limbs. More particularly, the present invention relates to an adaptor which can be fitted onto a prosthesis for the lower leg, so that the prosthesis may be secured to an ankle joint or prosthetic foot through a mechanical connection.

2. General Background

In the area of prosthetic limbs, one of the requirements in meeting the durability and wearability of the prosthesis is to assure that the lower limb prosthesis which would normally extend from the knee to the ankle may be secured on its lower end to a prosthetic foot while the upper end is accommodating the stump of the wearer. In the present state of the art, there are two general types of prostheses that are utilized. The first would involve a laminated type of lower limb prosthesis, and the second type would be a drape molded plastic prosthesis. In both cases, the prosthesis would accommodate the stump of the wearer in an upper cup portion, and the lower end would have a fixation means for attaching to an ankle joint or prosthetic foot. In the current state at the art, this fixation between the lower limb prosthesis and, for example, the prosthetic foot, would either be through clamping or a chemical bonding technique of gluing. Therefore, there is a need in the art for an attachment other than clamping or chemical bonding, such as gluing, which would allow a wearer to secure the lower end of the prosthesis to the ankle or foot.

SUMMARY OF THE PRESENT INVENTION

The apparatus of the present invention solves the problems in the art in a simple and straight forward manner. What is provided is an adaptor which may be secured to the lower end of a lower limb prosthesis which would allow the lower limb prosthesis to be secured to an ankle joint or prosthetic foot with a mechanical locking or anchoring type of fixation. What is provided is the lower limb prosthesis winch would include an upper socket portion for receiving the stump of the wearer, a limb portion which extends from the socket portion down to approximately the ankle portion of the wearer, and an adaptor portion. The adaptor portion would further include a triangulated base adaptor portion which would be mechanically secured to the lower end of the prosthetic ankle or foot. There would be further included a second barb portion extending upward from the base portion for securing to the lower end of the prosthetic limb, and would define an area between the barb portion and the base portion, so that when the adaptor is fabricated onto the limb through either a lamination process or a drape molding process, the adaptor is secured more firmly against the limb during the fabrication process. Further, there is included a threaded bushing secured within a bore of the base portion, for threadingly engaging the base portion to the upper end of the ankle and/or prosthetic foot of the wearer. Pinhole apertures are provided through the adaptor to place the channels in fluid communication with the interior of the adaptor. A vacuum applied to the interior of the adaptor sucks limb material deeper into the channels for a more secure anchorage by barbed shaped adaptor to the lower end of the prosthetic limb.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 2 is a side view of the adaptor portion of the apparatus of the present invention secured to the lower end of an artificial limb and also secured to the prosthetic foot of a wearer, in which the lower portion of the limb has been cut-away to reveal the adaptor portion that is internal thereto;

FIG. 5 is an enlarged view of the limb-and-adaptor structure shown in FIG. 2. with the adaptor shown in sectional view taken along the lines 5—5 of FIG. 3.

DETAILED DESCRIPTION OF THE PREFERRED EMBODIMENT

Figure 1:
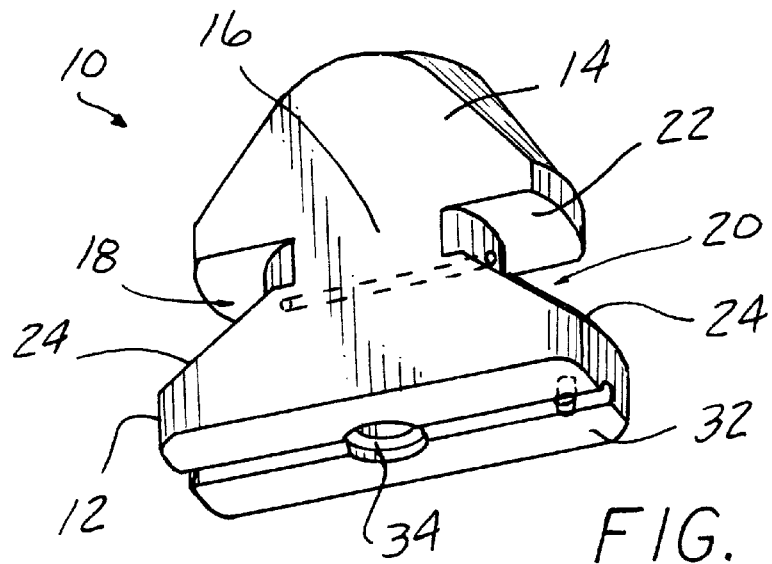
FIG. 1 is a perspective view of the adaptor portion of the apparatus of the present invention.
Figure 3:
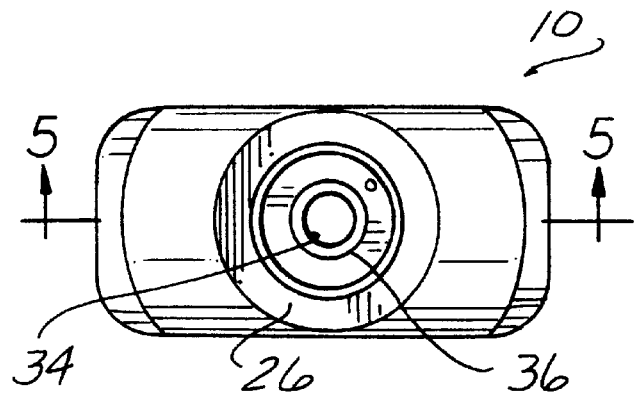
FIG. 3 is a top view of the adaptor portion of the apparatus of the present invention.
Figure 4:
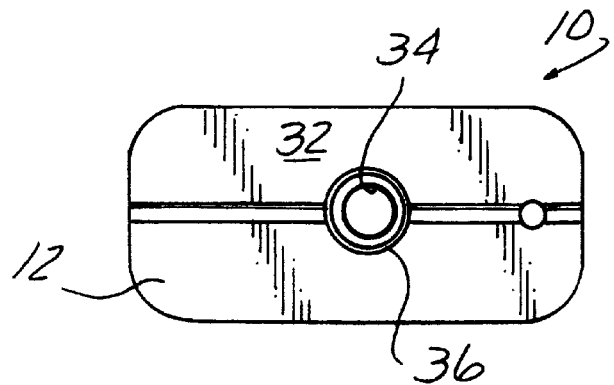
FIG. 4 is a bottom view of the adaptor portion of the apparatus of the present invention.

FIGS. 1 and 2 illustrate the preferred embodiment of the apparatus of the present invention by the numeral 10. As illustrated in FIG. 1 in overall perspective view, adaptor 10 as illustrated would be constructed of a molded plastic or the like, having a lower truncated triangular base portion 12 and an upper truncated triangular upper portion 14. The base portion 12 would be integral to the upper portion 14 along a central body connection 16, and would define double channels 18 and 20 between the lower face 22 of the upper portion 14 and the sloping walls 24 of the base portion 12. As further illustrated, the upper portion 14 would include an enlarged bore 26 which would extend substantially through the length of the upper portion 14, which would be utilized primarily for receiving the lower end 28 of a prosthetic limb 30 as will be discussed more fully in FIG. 2. As best seen in FIG. 4, the lower base portion 12 further includes a lower face 32 which would include a reduced diameter bore 34 therethrough, for accommodating a threaded collar or bushing 36, again, the function of which will be described further.

Turning now to FIG. 2, there is illustrated the prosthetic lower limb 30 the type which would be utilized by an amputee who would have generally lost the lower portion of his leg. As illustrated, the lower limb 30 on its upper portion would be of a typical construction, that is having an upper socket 40 for receiving the stump 42 (phantom view) of the wearer thereunto, a reduced diameter leg portion 44 extending downward from the socket 40 and terminating at lower end 28 substantially in the ankle area 45 of the wearer. As seen in FIG. 2, a bar 46 may be used during fabrication of limb 30 and is temporarily inserted into the enlarged bore 26 in the upper portion of the adaptor 10. The lower face 32 of the lower base portion 12 of the adaptor 10 is secured firmly against the upper portion 50 of a prosthetic foot or ankle 52 as illustrated, with a bolt member 54 extending from the foot 52 into the threaded bore 34 of the lower base portion 12 of the adaptor 10.

It is foreseen that in order to properly secure the adaptor 10 to the lower end 28 of the prosthetic limb 30, the adaptor 10 would be either laminated in place, were it to be a laminated prosthetic limb, or would be drape molded through the use of a plastic material, which would secure the adaptor 10 onto the lower end 28 of the prosthetic limb 30 as one integral laminated or molded plastic composite unit as shown in FIG. 2. In either event, in the fabrication of the adaptor 10 onto the lower end 28 of the prosthetic limb 10, whether it be through lamination or drape molding, the double channels or openings 18, 20, as discussed earlier, would serve to allow the plastic or lamination to fill channels 18 and 20 and to thereby pull the adaptor 10 more tightly onto the prosthetic limb 30 and secure it in place. It will be seen from FIGS. 2 AND 5 that the contours defined of adaptor 10 defined by channels 18, 20, base portion 12 and upper portion 14 form an anchor-like barb for securing adaptor 10 to the lower portion 28 of limb 30.

In this regard, pin hole apertures 56 and 58 are provided extending through central body 16 connection to place enlarged bore 26 in fluid communication with channels 18 and 20. In the embodiment of the invention shown in FIG. 5, apertures 60 and 62 are also placed through the sidewall 64 of bar 46 and are aligned with apertures 56 and 58, respectively so that sidewall 64 does not block the fluid communication between channels 18 and 20 and bore 26 via apertures 56 and 58. Once limb 30 has been fabricated, bar 46 may be removed.

During construction of limb 30, a vacuum force may be applied internal to the limb 30 to create a vacuum or reduced pressure inside bore 26. Because channels 18 and 20 are in fluid communication with bore 26, the vacuum force sucks lamination and drape molding (as the case may be) material forming lower end 28 into channels 18 and 20, thus providing a more secure encasement of adaptor 10 within the lower portion of 28 of limb 30.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed is:

1. A prosthetic adaptor comprising:
    a hastate body having interconnected first and second portions defining at least one channel therebetween for receiving a pliable material forming a prosthetic limb to be attached thereto, an internal bore extending through at least part of the first portion of the body, and at least one aperture extending through one of the first portion and the second portion for placing the channel in fluid communication with the bore to enable at least a portion of the pliable material forming the prosthetic limb to enter the channel and the bore.
2. The adapter of claim 1 wherein the first portion and the channel define a barb.
3. The adapter of claim 1 wherein the second portion includes attaching means for attaching a prosthetic limb component to be assembled thereto.
4. The adapter of claim 3 wherein the attaching means includes a threaded bore adaptor for receiving a bolt coaxial with the internal bore of the body.
5. The adaptor of claim 1 wherein the first portion includes a lower face and the second portion includes an upper face spaced apart from the lower face of the first portion to define the channel.
6. The adaptor of claim 1 wherein the first and second portions define two channels.
7. The adaptor of claim 1 wherein the aperture is a pin-hole aperture.
8. A prosthetic limb adaptor comprising:
    a body defining at least one channel for receiving a portion of plastic material forming a first limb component to be connected thereto, a bore extending along a central axis of the body from an anticline through at least part of the body, and at least one aperture extending through the body and placing the channel in fluid communication with the bore.
9. The adaptor of claim 8 wherein the body includes a barbed portion, a base portion and an interconnecting portion between the barbed portion and the base portion.
10. The adaptor of claim 9 wherein the bore extends through the barbed portion.
11. The adaptor of claim 9 wherein the aperture extends through the interconnecting portion.
12. The adaptor of claim 8 wherein the body defines a plurality of channels.
13. The adaptor of claim 8 further comprising means for attaching a second limb component to the body.
14. The adaptor of claim 13 wherein the attaching means includes a threaded bore coaxial with the bore of the body.
15. The adaptor of claim 8 wherein the aperture is a pinhole aperture.
16. The adaptor of claim 8 wherein the plastic material is a laminate material.
17. The adaptor of claim 8 wherein the plastic material is a drape molded material.
18. A prosthetic device for connecting a prosthetic foot to an amputee comprising:
    a lower limb prosthesis having an upper stump-engaging socket, the lower limb prosthesis being formed of a plastic material; and
    an adaptor having a hastate body contoured to define at least one exterior channel, an inner bore extending along a central axis of the body from an anticline through at least part of the body, at least one aperture through the body placing the channel in fluid communication with the inner bore, and attaching means for attaching a prosthetic foot to the adaptor, wherein at least a portion of the adaptor is encased in the plastic material of the lower limb prosthesis so that at least a portion of the plastic material is disposed in the channel.
19. The prosthetic device of claim 18 wherein the attaching means includes a threaded aperture coaxial with the inner bore of the body.
20. The prosthetic device of claim 18 wherein the body includes a barbed portion, a base portion and an interconnecting portion between the barbed portion and the base portion.
21. The prosthetic device of claim 20 wherein the bore extends through the barbed portion.
22. The prosthetic device of claim 20 wherein the aperture extends through the interconnecting portion.
23. The prosthetic device of claim 18 wherein the body defines a plurality of channels.
24. The prosthetic device of claim 18 wherein the aperture is a pinhole aperture.
25. The prosthetic device of claim 18 wherein the plastic material is a laminate material.
26. The prosthetic device of claim 18 wherein the plastic material is a drape molded material.

* * * * *